United States Patent [19]

Lee

[11] 4,125,117
[45] Nov. 14, 1978

[54] EXTERNAL BREAST PROSTHESIS

[76] Inventor: Denis C. Lee, 1120 Heatherway, Ann Arbor, Mich. 48104

[21] Appl. No.: 836,533

[22] Filed: Sep. 26, 1977

Related U.S. Application Data

[63] Continuation-in-part of Ser. No. 769,115, Feb. 16, 1977, abandoned; which is a continuation of Ser. No. 664,234, Mar. 5, 1976, abandoned; which is a continuation-in-part of 605,031, Aug. 15, 1975, abandoned.

[51] Int. Cl.² .............................................. A41C 3/10
[52] U.S. Cl. .................................... 128/481; 128/478
[58] Field of Search ............... 128/481, 462, 478, 479, 128/480, 505, 360, 150; 3/36

[56] References Cited
U.S. PATENT DOCUMENTS

| | | | |
|---|---|---|---|
| 2,698,436 | 1/1955 | Bernhart | 3/36 |
| 3,304,558 | 2/1969 | Mann | 128/481 |

Primary Examiner—Doris L. Troutman
Attorney, Agent, or Firm—Wood, Herron & Evans

[57] ABSTRACT

To provide a univeral breast prosthesis usable as a substitute for either the right or left breast and for patients who have had varying degrees of surgery, scarring, muscle removal and the like, a breast prosthesis is provided having an upper flap and symmetrical lateral flaps. The upper flap is designed to cover subclavicular defects of varying degrees and can be trimmed as desired depending on the nature and extent of the defect to be covered. Similarly, the opposite lateral flaps are designed to cover sternum and underarm defects, and each can be separately trimmed depending upon the nature and extent of the respective defects.

24 Claims, 11 Drawing Figures

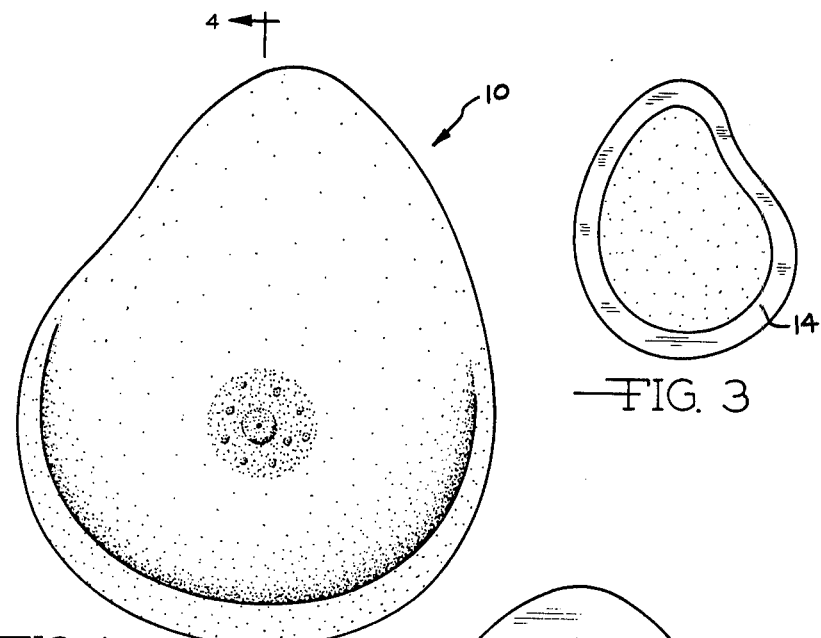
FIG. 1
FIG. 3
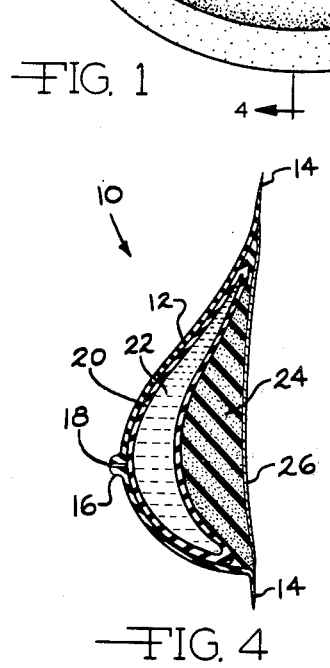
FIG. 4
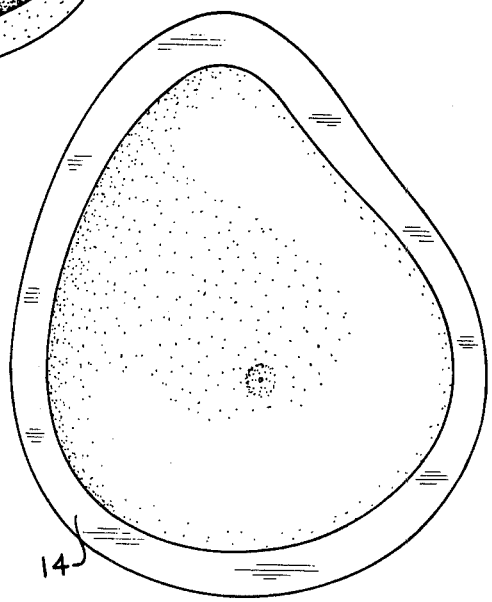
FIG. 2

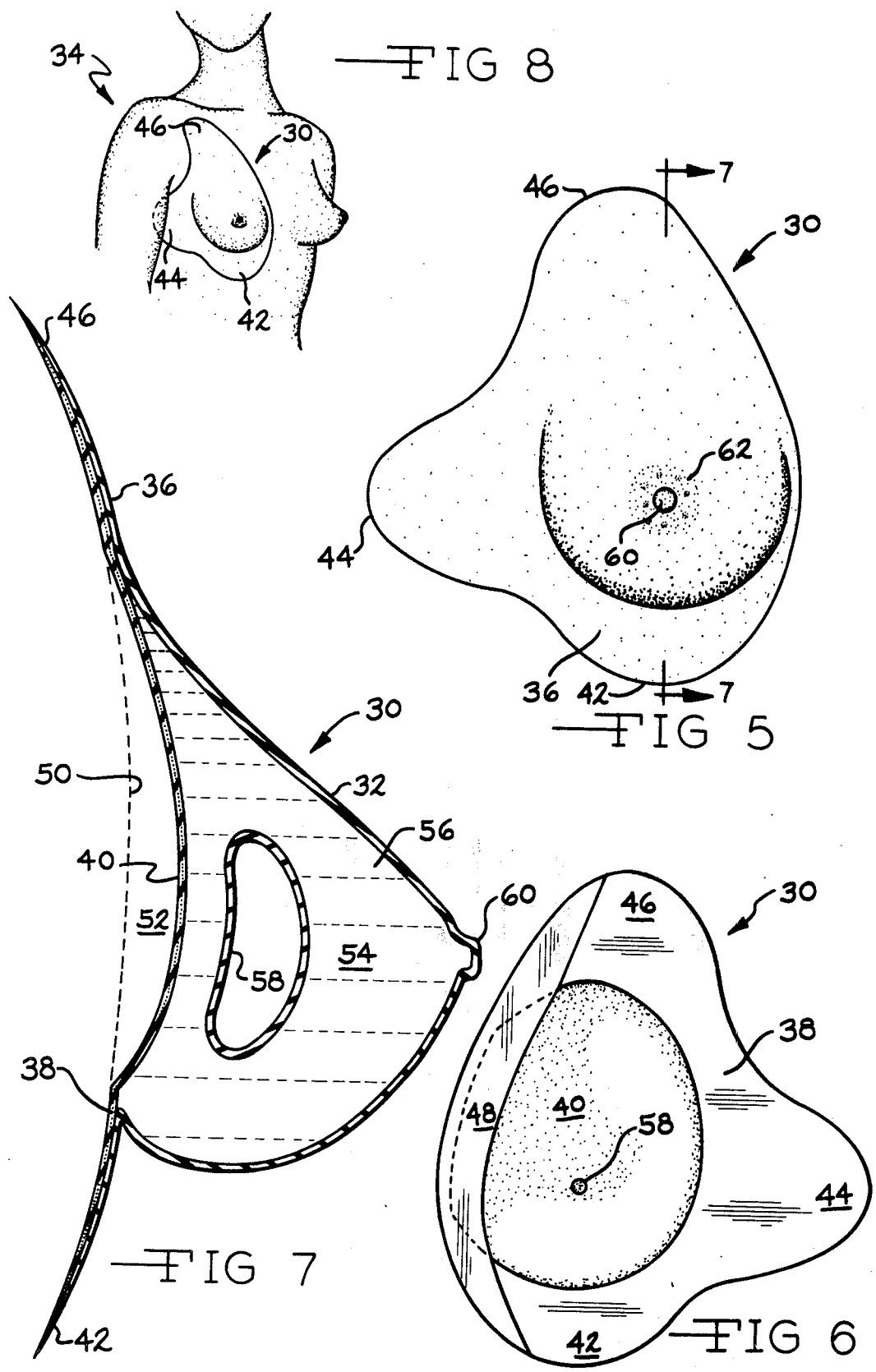

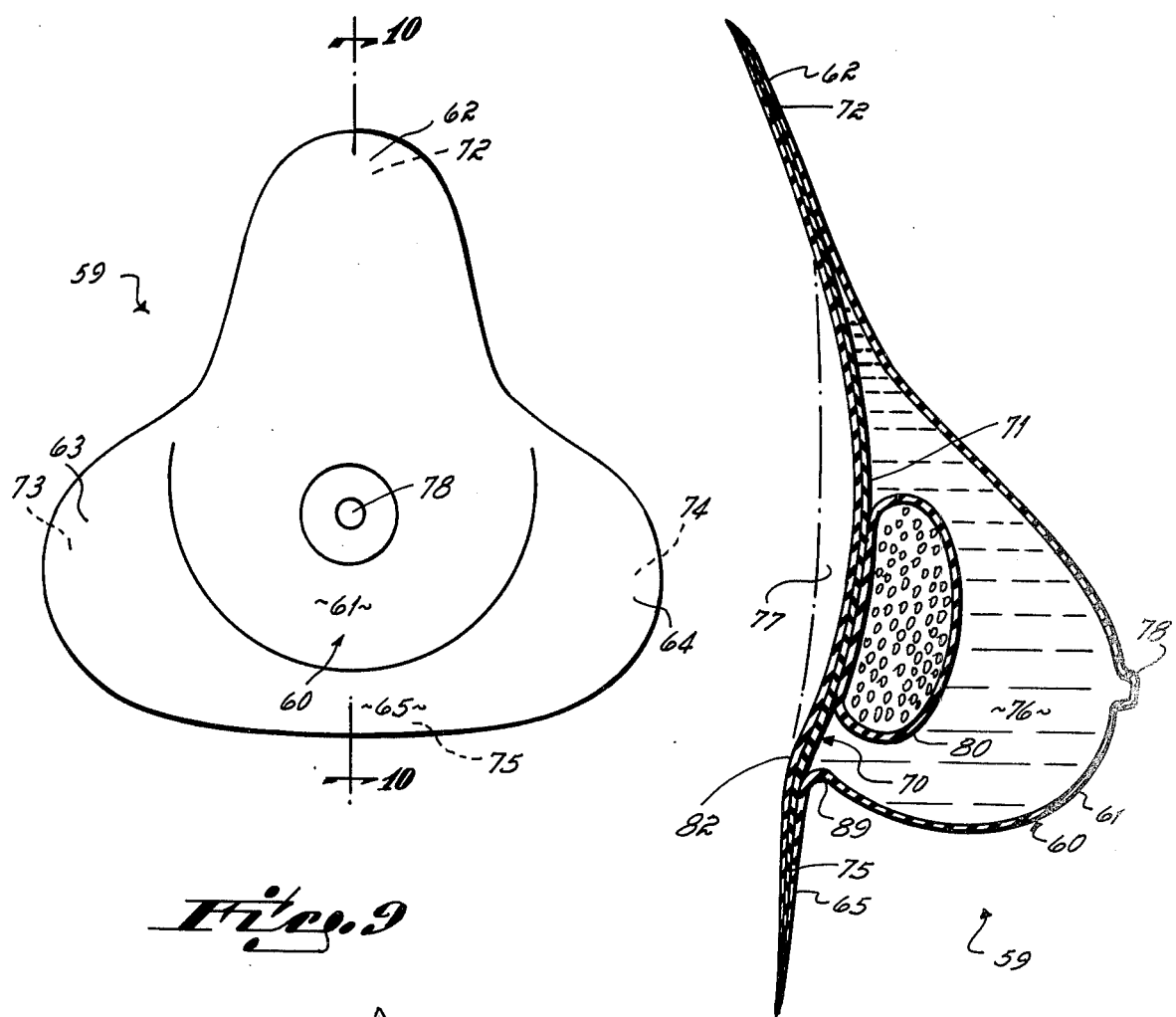
Fig.9
Fig.10
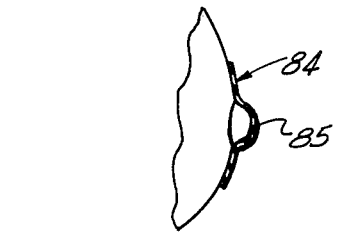
Fig.11

EXTERNAL BREAST PROSTHESIS

REFERENCE TO RELATED APPLICATIONS

This application is a continuation in part of prior application Ser. No. 769,115, filed Feb. 16, 1977, now abandoned; which is a streamlined continuation of Ser. No. 664,234, filed Mar. 5, 1976, now abandoned; Ser. No. 664,234 in turn was a continuation in part of prior application 605,031, filed Aug. 15, 1975, now abandoned.

BACKGROUND OF THE INVENTION

The present invention relates to an external breast prosthesis primarily adapted for mastectomy patients.

Prostheses of this character now available are basically fillers or pads for bras that are made out of many materials, including silicone rubber. There prior prostheses have not been fully satisfactory.

Previous attempts have been made to produce a satisfactory prosthesis which could be attached to the chest wall, but these attempts have been unsatisfactory for several reasons. Often the product was too heavy for available adhesives; the weight or contact that was made irritated surgical areas of the chest wall; and the entire back of the prosthesis had to be glued to the chest wall, thus requiring it to be custom made and generally causing discomfort to the patient.

SUMMARY OF THE INVENTION

The present invention has overcome the inadequacies of the prior art and provides an improved breast prosthesis which is characterized by its improved construction and its more natural appearance and feel to the patient. The improved prosthesis can be manufactured easily to match the normal remaining breast of the patient in size, color and weight. It may be attached to the chest wall with medical adhesive allowing it to be worn for long periods of time, and it can be worn to bed and in the water. It may also be worn in the bra without adhesive. Further, the prosthesis is constructed and arranged so as to avoid acting as a source of discomfort to the patient in the surgical area of the mastectomy.

According to one form of the present invention an external breast prosthesis is provided which comprises a thin flexible shell of an elastomeric material contoured to conform to the configuration of the breast of a mastectomy patient and having a rear peripheral edge for attachment by an adhesive to the chest wall of the patient, and a filler retained within the confines of the thin shell having soft flexible physical characteristics. In one form a flexible foam plastic material is bonded to the flexible shell adjacent to the peripheral edge thereof and in cooperation with the shell confines the filler within an anterior chamber of the prosthesis. The flexible foam plastic material forms a concave rear wall portion within the peripheral edge to give the edges of the prosthesis more flexibility for fit and in some instances to help in adhering the prosthesis to the skin with suction. The concave rear wall or portion provides a layer or chamber of air over the surgical area of the mastectomy to minimize contact of the prosthesis with the surgical area, thereby avoiding irritation to the patient, particularly during early periods after the surgery. A sheepskin backing may be provided on the rear wall of the flexible foam plastic material or within the air chamber to aid in reducing perspiration. An air hole is provided in the nipple to permit limited flow of air into and out of the thin flexible shell, and the thin flexible shell can be colored to match the skin of the patient.

Several suitable types of fillers can be employed, including bags of silicone and glycerin, silicone foam or gel pads, or silicone bags filled with air. The prosthesis can be attached to the chest wall with a very strong silicone adhesive or double sided adhesive tape which is non-toxic and hypo-allergenic. If a patient desires, the adhesive can be omitted, and the suction characteristics of the prosthesis can be utilized to aid in retaining the prosthesis against the chest wall of the patient when the prosthesis is worn with a bra.

Other forms of the invention may utilize a modified concave rear portion which is constructed of the same elastomeric material as the thin flexible shell and which may include a thin reinforcing fabric. In a preferred form of the invention the shell and the concave rear portion are made of a silicone elastomer, each having a thickness of about one millimeter. The rear portion can be reinforced by embedding a nylon fabric thereon. In this form of the invention the peripheral edges include inferior, lateral, superior and medial flaps for attachment to the chest wall of the patient for improved holding purposes and to conceal radical surgery defects that may have occurred. This form of the invention can be produced and sold in standard sizes and, if desired, the flaps can be trimmed or used in the manner best serving the needs of the patient.

The prosthesis can be constructed so that it is available in standard breast sizes in a variety of color tones to enable the patient to order a prosthesis by mail from a set of patterns and colors that have previously been made available to the patient.

To enhance the ease with which the prosthesis can be adhered to the chest of the user when the prosthesis is fabricated of silicone, the rear surface of the prosthesis is provided with a backing layer of acrylic polymer emulsion. The acrylic polymer emulsion backing, which can be adhered to the rear of a silicone prosthesis with a suitable silicone adhesive, provides a non-silicone surface which can be adhered to the chest of the user utilizing commercially available double-sided non-silicone adhesive tape. Adhering the prosthesis to the chest wall with double-sided tape has been found to be far more convenient than using silicone adhesive which is expensive and difficult to remove from skin and prosthesis.

An advantage of this invention attributable to forming the front of the prosthesis with flexible material approximately 1 millimeter thick is that a mammary fold is produced underneath the breast simulating the sag often found in a normal breast.

Thus, it is an object of the present invention to provide an improved external breast prosthesis which more nearly meets the requirements of mastectomy patients than was possible heretofore when utilizing prior art devices of this character.

Other objects of this invention will appear in the following description and appended claims, reference being had to the accompanying drawings froming a part of this specification wherein like reference characters designate corresponding parts in the several views.

BRIEF DESCRIPTION OF THE DRAWINGS

FIG. 1 is a front elevational view of one form of an external breast prosthesis embodying the present invention;

FIG. 2 is a rear elevational view of the thin flexible shell of the breast prosthesis illustrated in FIG. 1;

FIG. 3 is a rear elevational view in reduced scale of the breast prosthesis illustrated in FIG. 1;

FIG. 4 is a section in reduced scale taken on the lines 4—4 of FIG. 1;

FIG. 5 is a front elevational view of another form of an external breast prosthesis embodying the present invention;

FIG. 6 is a rear elevational view of the form shown in FIG. 5;

FIG. 7 is an enlarged section taken on the lines 7—7 of FIG. 5;

FIG. 8 is a fragmentary illustration in reduced scale of a mastectomy patient wearing the form of the external breast prosthesis shown in FIG. 5;

FIG. 9 is a front elevational view of a modified breast prosthesis incorporating certain additional principles of this invention;

FIG. 10 is a cross-sectional view taken along line 10—10 of FIG. 9; and

FIG. 11 is a vertical cross-sectional view of a nipple prosthesis suitable for use in modifying the nipple of the breast prosthesis of this invention.

DESCRIPTION OF THE PREFERRED EMBODIMENT

Before explaining the present invention in detail, it is to be understood that the invention is not limited in its application to the details of construction and arrangement of parts illustrated in the accompanying drawings, since the invention is capable of other embodiments and of being practiced or carried out in various ways. Also, it is to be understood that the phraseology or terminology employed herein is for the purpose of description and not of limitation.

Referring now to the drawings, the embodiment of the invention illustrated in FIGS. 1-4 will first be described. The external breast prosthesis 10 is adapted for use primarily by mastectomy patients and comprises a thin flexible shell 12 of a suitable elastic material, such as silicone rubber, which has been contoured to the configuration of the breast and has a rear peripheral edge 14 for attachment by a suitable adhesive to the chest wall of a patient. The thin flexible shell has a nipple 16 through which an air hole 18 passes to permit passage of air.

A filler 20 is located within the thin flexible shell 12 and is constructed of suitable material having soft flexible physical characteristics. The filler can be suitably constructed in the form of a bag of silicone or glycerin to add weight and bounce to the prosthesis. Also, a silicone foam or gel pad may be used or a silicone bag can be constructed which is filled with air.

In this embodiment of the invention the filler 20 is a silicone bag containing fluid glycerin 22. A flexible foam plastic material 24, such as silicone foam, is introduced during manufacture into the back of the flexible shell and is bonded thereto so as to confine the filler 20 within the anterior chamber of the prosthesis. The rear portion 24 of the prosthesis 10 is concave to give the edges of the prosthesis more flexibility for fit and to help adhere the prosthesis to the skin through suction action and also to permit an air chamber or air layer to exist, if desired, between the back portion 24 and the surgical area of the mastectomy. A sheepskin backing 26 is provided on the rear side of the silicone foam for reducing perspiration.

If desired, the thin edge 14 of the prosthesis can be reinforced with nylon, dacron, vinyls or stronger silicone rubbers, depending upon the weight of the prosthesis.

Referring to FIGS. 5-8, the embodiment of the invention illustrated in these figures will now be described. The external breast prosthesis 30 includes the thin flexible shell 32 of a thin elastomeric silicone material contoured to conform to the breast of the patient 34 and having a peripheral edge 36 extending around the entire periphery of the shell 32. A thin flexible backing member 38 is secured to the peripheral edge to form an integral part of the peripheral edge and includes a concave rear portion 40 within the confines of the peripheral edge 36. The integrally connected shell 32 and backing member 38 are dimensioned to form an inferior flap 42, a lateral flap 44 and a superior flap 46, each of which extends away from the concave rear portion 40, and a medial flap 48 which extends inward toward the concave portion 40, as seen best in FIG. 6. These flaps are adapted to be attached by a suitable adhesive to the chest wall 50 of the patient, and the concave rear portion 40 is dimensioned so that when the flaps forming the peripheral edge 36 are attached, the rear concave portion 40 will define an air layer or air chamber 52 over the surgical area of the mastectomy.

The shell 32 and the concave rear portion 40 also define between them an anterior chamber 54 in which a fluid material 56, which in this instance is glycerin, is confined. For the purpose of reducing the weight of the prosthesis 30, a bag 58 of a silicone elastomer filled with air is permitted to float in the glycerin.

The present invention is much easier and less expensive to produce than prior art devices. A one piece mold is all that is required to produce the entire prosthesis. This mold can be made of plaster, clay, organic plastic material or metal because no heat is necessary with certain silicone. A tough, room temperature vulcanizing silicone is colored and poured or sprayed into the mold. This dries quickly at room temperature. The silicone bag 58 filled with air or any other fill may be added at this stage of the process. Then a piece of reinforcement material such as nylon is dipped into a liquid RTV silicone adhesive and laid on the previous coat of silicone lying flat against the peripheral edge 36 and associated flaps to create the anterior chamber 54 between the two layers of silicone, and the nylon reinforced backing member 38 will be allowed to sag down into the concavity of the mold approximately 1 cm. creating a concavity on the back of the prosthesis simultaneously. When this layer 38 dries, glycerin 56 is injected through the reinforced layer 38 into the anterior chamber 54. The injection site 58 is then sealed with RTV medical adhesive and allowed to dry. Air bubbles may be removed with a syringe, sealing the layer 38 again in the same manner. When the seals have dried, the prosthesis is removed from the mold and trimmed to the desired shape. The prosthesis is finished.

This prosthesis is most satisfactory because the outer skin can be made very thin, within the range of 1-2 mm., because of its strength and elasticity. This is significant, because it allows the prosthesis to sag and move substantially the same as the normal breast. The concave back is important because the patient's surgical area is not touched or irritated by the prosthesis. It provides space for antiperspirant pads such as sheepskin to be inserted if desirable. These pads are optional and not attached to the prosthesis. The concave back also may provide a partial vacuum chamber which may help retain the prosthesis in place when worn in the bra without adhesive.

The prosthesis is attached to the chest wall by applying adhesive to the peripheral margin and pressing it into place. This thin flexible margin is important. The thin flexible edge allows one prosthesis to fit any chest wall so that this prosthesis can be mass produced and sold as a stock item. For example, all women of a certain age who wear a 36C bra can wear the same prosthesis no matter how disfigured their chest wall may be from radial cancer surgery.

The four flaps incorporated into the peripheral edge are important. Each flap has a specific purpose. The inferior flap 42 extends down approximately two inches depending on the size of the prosthesis. This flap is designed to fit under the lower band portion of the bra and prevents the bra from riding up when the arm is lifted. This is one of the chief complaints of women who wear prostheses which are not attached to the chest wall. The lateral flap 44 is important, because it functions in an area of the body which receives the most movement. Therefore, this flap is large and extends under the arm of the patient at least 6 inches to secure the prosthesis adequately, and also to cover radical surgery defects under the arm. The superior flap 46 supports mots of the weight of the prosthesis, and it also extends upward to cover subclavicular defects left by radical mastectomies and for this purpose should be about 8 inches in length. The medial flap 48 is unique in that it may be extended under so that it may be trimmed so as to be not visible in low cut garments. All four flaps may vary with the size of the prosthesis and may be trimmed to fit each patient's individual needs, but as stock items the inferior flap 42 should be at least 2 inches in length, the lateral flap 44 should be at least 6 inches in length and the superior flap 46 should be at least 8 inches in length.

Each prosthesis 30 has a nipple 60 and areola 62 which can be tinted to match the patient's coloring. Standard prosthesis 30 would be available in three to five basic colors for all races. As indicated above, silicone elastomers are suitable materials for use in forming the shell 32 and the backing member 38. The backing member 38 and adhesive materials may be a medical adhesive silicone Type A sold by Dow Corning Corporation under its trademark SILASTIC, and the shell 32 can be a silicone elastomer of the type sold by Dow Corning Corporation as SILASTIC RTV Silicone Rubber or a heat vulcanizing silicone rubber may be used.

From the foregoing description it would be understood that the prosthesis can be made available in standard breast sizes which can be maintained as a stock item in a supply house, and the patient after receiving a set of patterns and colors can order the appropriate prosthesis to meet her needs. This will enable a prosthesis to be obtained which will match the color and skin of the patient, and the prosthesis can be adhered to the chest wall of the patient so that it will have a natural appearance and will have normal flexibility in movement.

With reference to FIGS. 9 and 10, a modified version 59 of the breast prosthesis of this invention is shown which includes a front membrane or sheet 60, preferably fabricated of silicone, having a convex central portion 61 simulating the shape of the wearer's removed breast, an upper flap 62, a pair of oppositely directed lateral flaps 63 and 64, and a lower flap 65. When the prosthesis 59 is properly positioned on the chest of the mastectomy patient, the upper flap 62 extends upwardly, covering suclavicular defects, e.g., defects resulting from a radical mastectomy of either the right or left breast where part or all of the pectoralis muscle has been removed. With the prosthesis 59 properly positioned, and assuming the prosthesis is used as a replacement for the right breast, the lateral flap 63 extends under the wearer's right arm to cover lateral defects, e.g., defects resulting from a radical mastectomy where there has been dissection of the lymph nodes, muscles and body tissues. Assuming a right mastectomy was performed, when the prosthesis 59 is properly positioned, the lateral flap 64 covers defects in the center of the chest or sternum resulting from the surgery. Obviously, if the prosthesis 59 is used as a substitute for the left breast, the lateral flap 64 will underlie the left arm, covering lateral defects proximate thereto, while the lateral flap 63 will extend to and cover defects in the center of the chest. The lower flap 65, whether the prosthesis is used as a substitute for the right or left breast, is designed to extend downwardly between the chest wall and the lower portion of the bra beneath the cup thereof such that it is sandwiched between the wearer's chest and the under-cup region of the bra. This anchors the prosthesis and prevents it from riding up on the wearer's chest.

The prosthesis 59 also includes a rear sheet or membrane 70, preferably silicone, which has a central concave portion 71, an upper flap 72, opposite lateral flaps 73 and 74, and a lower flap 75. The upper, lateral and lower flaps 72, 73, 74 and 75 are coextensive in size and identical in shape to the flaps 62, 63, 64 and 65. Flaps 62, 63, 64 and 65 are adhered to flaps 72, 73, 74 and 75, respectively, by a suitable adhesive to render the cavity 76 fluid-tight. If sheets 60 and 70 are silicone, Dow Corning 1200 silicone primer can be used as the adhesive.

The central section 71 of the rear sheet 70 forms the base, or rear wall, of the central concave front section 61 and in combination therewith forms a sealed cavity 76 which is filled with liquid, such as glycerin, silicone, or the like. The concave central section 71 of the rear panel or membrane 70 is designed to overlie the chest wall in the region of the removed breast. The concave shape of the central section 71 of the rear membrane 70, when placed over the chest wall in the region of the removed breast, forms a cavity, or rear recess 77. The cavity 77 prevents the central rear portion of the prosthesis 59 from rubbing or chafing against the chest wall in the region of the removed breast, which is normally quite tender and susceptive of irritation. If desired, a pad of urethane foam or lambs' wool can be inserted in the cavity 77.

Alternatively, the cavity 77 can be left empty to form an air chamber between the rear portion of the prosthesis 59 and the chest wall of the wearer in the region of the removed breast to function as an air cushion or shock absorber. The resulting air cushion in the empty cavity 77, in addition to providing cushioning, or shock absorbing, action, also provides the prosthesis with a realistic degree of "bounce" simulating a natural breast. If the cavity 77 is left empty, air circulation is enhanced over the wearer's chest wall in the region of the removed breast, promoting the evaporation of perspiration. Finally, by not filling the cavity 77 with a cushioning pad or the like, the empty cavity 77 can be used to promote adherence of the prothesis to the chest wall by suction action.

A completely enclosed sac or baloon 80, also fluid-tight, is attached to the central section 71 of the rear panel 70 by a suitable adhesive. The sac 80, unlike the cavity 76 which is filled with a liquid, is filled with a gas. By varying the size of the gas-filled sac 80, the overall weight, shape and volume of the prosthesis can be varied. This permits adjustment for symmetry relative to the other breast, whether natural or artificial.

If the rear sheet 70 of the prosthesis 59 is fabricated of silicone, the rear surface thereof is preferably provided with a backing layer 82 in the form of an acrylic polymer emulsion which is bonded to the rear surface of the sheet 70 with a suitable silicone adhesive such as Dow Corning 1200 silicone primer. The acrylic polymer emulsion backing layer 82 permits the prosthesis 59 to be conveniently adhered to the chest wall with double-sided non-silicone adhesive tape such as double-coated medical tape 1522 manufactured by 3M Corporation. This is in lieu of using silicone adhesive which is messy and significantly more time-consuming.

In use, and by virtue of the symmetry of the prosthesis, the prosthesis can be used as a substitute for either the right or left breast prosthesis. In practice, the flaps 62-72, 63-73 and 64-74 are cut or trimmed with a scissors as desired to cover the sternum, subclavicular and lateral defects of the particular wearer. Obviously, the degree to which the flaps are trimmed will depend upon the nature and extent of surgery. For example, if a right mastectomy was not radical, and there are no lateral defects, the lateral flap 63 may be trimmed or removed in its entirety since there is no scar tissue in the area of the lymph nodes and muscles in the right underarm region.

Typically, the central portion 61 of the front membrane or sheet 60 will be provided with a protuberance 78 to simulate the nipple. If the prosthesis 59 is made in standardized sizes and the nipple 78 thereof is smaller than desired, a circular overlay sheet 84 having a convex central section 85 in the shape of the desired nipple of increased size can be provided. The overlay 84, if fabricated of the same material as the front sheet 60, such as silicone, will cohere to the front sheet 60 without adhesive and remain properly positioned. Alternatively, the overlay 84 could be bonded to the front sheet 60 with a suitable cement or glue such as silicone adhesive. If a separate overlay nipple 84 is utilized, a small aperature is preferably provided in the front central portion thereof to permit the nipple to collapse under pressure, such as when contained by a bra, in much the same fashion that a natural nipple compresses when pressure is directed to the exterior thereof. Of course, upon removal of pressure, the collapsed nipple 85 of the overlay 84 would return to its normal uncollapsed condition.

The prosthessis 59 can be fabricated by applying a thin layer of elastomeric material, such as silicone rubber, polyvinyl chloride, urethane, or like plastic in liquid form, using a paint brush, spray or the like, to a negative mold of the breast. For example, a one millimeter thick layer of Silastic brand 732 RTV silicone rubber available from Dow Corning Corp., Midland, MI, which is described in Bulletin 61-015b dated May, 1972, has been found satisfactory. To facilitate convenient brushing of the paste onto the mold surface, the paste can be diluted with xylene or other solvent to achieve the desired viscosity. The silicone is allowed to set in the mold at room temperature for 1-2 hours, forming the front membrane 60.

The air sac 80 may be fabricated separately. Specifically, a negative mold having a shape corresponding to that of the air sac is coated with a thin layer of acrylic polymer emulsion of approximately 1 millimeter thickness and allowed to dry to form a cup-shaped shell. The mouth or surface of the cup-shaped acrylic polymer emulsion shell is then sealed by coating it with silicone adhesive. Then covering the mouth and surface with a fabric sheet which has previously been impregnated with silicone adhesive. The impregnated fabric portion of the air sac 80 covering sac is removed then adhered with silicone adhesive to the shell flaps 60 in the mold. The sac that has been been reversed with the acrylic outside is then sealed with a sheet of acrylic using liquid acrylic as an adhesive.

The fabric forming the rear sheet 71 should have sufficient threads per inch to hold the silicone adhesive without creating holes in the rear sheet.

When the rear sheet 71 has been impregnated and applied to the front membrane 60 in the manner indicated, the cavity 76 is formed. To fill the cavity 76 with a suitable liquid, a small incision is made with a scalpel or like tool and the cavity is filled with glycerin, liquid silicone or like material using a funnel. To assure concavity of the rear sheet 70, the cavity 76 should not be over-filled. The opening in the rear sheet 70 and 82 is sealed by applying a patch of fabric to the rear sheet 70 in the region of the opening. The acrylic patch is adhered to the rear sheet 70 with silicone adhesive such as Silastic brand medical adhesive Type A paste available from Dow Corning Corp., described in Bulletin 14-398, dated January, 1970. After the adhesive has dried, a layer of acrylic is applied to the rear of the patch, enhancing the silicone impregnation of the patch.

With the prosthesis cavity 76 filled with silicone liquid, the prosthesis is suspended from the upper edge of the upper flap 62-72, allowing entrapped air to rise. A syringe is inserted into the prosthesis in the region of the air bubble to vent the air. Upon removal of the syringe, silicone adhesive is applied to the hole formed by the syringe to seal it.

An acrylic polymer emulsion backing sheet 82 may be formed by applying a coating of liquid acrylic polymer emulsion, preferably 1 millimeter thickness or less, to a flat metal surface. After allowing the acrylic polymer emulsion to dry at room temperature for approximately 8 hours or more, the dry acrylic polymer emulsion sheet is peeled off the metal surface and adhered to the back of the rear sheet 70 using silicone adhesive and allowed to dry.

By virtue of using acrylic backing sheet 82, the flaps 72, 73, 74 and 75 can be adhered to the chest wall of the wearer with double-sided tape, as noted previously. This dispenses with the need to use silicone adhesive, which is messy, as would otherwise be required were the acrylic polymer emulsion sheet omitted and the rear sheet 70 adhered directly to the wearer's chest.

The nipple overlay 84 is preferably fabricated of silicone by applying a coating of liquid silicone, having a thickness in the approximate range of 1-5 millimeters, preferably 1 millimeter thick, to a negative mold and allowed to dry in much the same manner that the front membrane 60 of the prosthesis 59 is fabricated.

The volume of the air sac 80 can be altered by injecting a hypodermic needle into it via the sheet 82. Upon withdrawal of the hypodermic needle, the opening in the sheets 82 and 70 left by the hypodermic needle is sealed using acrylic and an acrylic-impregnated fabric patch in a manner described previously in connection with sealing the opening left by withdrawal of the syringe used to remove air from the cavity 76. Preferably, the volume of the air sac 80 is approximately 25% of the volume of the cavity 76. As noted, by varying the extent of inflation of the air sac 80, the shape, weight and volume of the breast prosthesis 59 can be varied as desired to assure symmetry and and balance with respect to the other breast.

By virtue of utilizing a front sheet 60 of flexible silicone material having a thickness in the approximate range of 1–5 millimeters, preferably approximately 1 millimeter, a fold 89 results underneath the breast where the front membrane 60 joins the rear sheet 70. The fold 89 enhances the realism and naturalness of the appearance of the prosthesis, simulating the sag of a normal breast.

What is claimed is:

1. An external breast prosthesis primarily for mastectomy patients comprising a thin flexible shell of an elastomeric material contoured to conform to the configuration of the breast of the patient and having a peripheral edge extending around the entire periphery of said shell for attachment by an adhesive to the chest wall of the patient and a filler retained within the confines of said thin shell having soft flexible physical characteristics, said shell having a rear portion that is concave within the confines of said peripheral edge so that the prosthesis can be attached at said peripheral edge to the chest wall of a patient to provide within the peripheral edge a chamber of air over the surgical area of the surgical area of the mastectomy, said peripheral edge including an inferior flap, a lateral flap, a superior flap and a medial flap, said inferior, lateral and superior flaps extending in directions away from said concave rear portion and said medial flap extending inward toward said concave rear portion.

2. The external breast prosthesis that is defined in claim 1, wherein said peripheral edge includes an inferior flap, a lateral flap, a superior flap and a medial flap, said inferior, lateral and superior flaps extending in directions away from said concave rear portion and said medial flap extending inward toward said concave rear portion.

3. The external breast prosthesis that is defined in claim 1 wherein said inferior flap extends at least 2 inches away from said concave rear portion, said lateral flap extends at least 6 inches away from said concave rear portion, and said superior flap extends at least 8 inches away from said concave rear portion.

4. The external breast prosthesis that is defined in claim 1 which includes a flexible sheet material bonded to said flaps and forming a part of said peripheral edge, said flexible sheet material defining said concave portion.

5. The external breast prosthesis that is defined in claim 4 wherein said filler is glycerin.

6. The external breast prosthesis that is defined in claim 5 wherein a silicone bag containing air is located in said filler.

7. The external breast prosthesis that is defined in claim 1 wherein said filler is a silicone.

8. The external breast prosthesis that is defined in claim 1 wherein filler is a gel material.

9. The external breast prosthesis that is defined in claim 1 wherein an adhesive that is non-toxic and hypoallergenic is provided for attaching said peripheral edge to the chest wall of the patient.

10. An external breast prosthesis for mastectomy patients comprising a thin flexible shell of an elastomeric material contoured to conform to the configuration of the breast of the patient and having a peripheral edge extending around the entire periphery of the shell, a thin flexible backing member secured to the peripheral edge of said shell and providing a concave rear portion within the confines of the peripheral edge, said shell and said backing member being dimensioned to form an inferior flap, a lateral flap and a superior flap extending away from said concave rear portion, and a medial flap extending inward toward said concave rear portion, said flaps being adapted to be attached by an adhesive to the chest wall of the patient and the concave rear portion being dimensioned so that when the flaps are attached the concave rear portion will define an air chamber over the surgical area of the mastectomy, said shell and said concave rear portion defining an anterior chamber, and a fluid material confined within said anterior chamber.

11. The external breast prosthesis that is defined in claim 10 wherein said shell and said backing are a silicone elastomer and each has a thickness of about 1 millimeter.

12. The external breast prosthesis that is defined in claim 11 wherein said backing member has embedded therein a reinforcing fabric.

13. The external breast prosthesis that is defined in claim 10 wherein said fluid material is glycerin.

14. The external breast prosthesis that is defined in claim 13 wherein said anterior chamber contains a silicone elastomer bag filled with a gas, said bag floating in said glycerin.

15. An external breast prosthesis primarily for mastectomy patients comprising:
   a thin flexible fluid impervious shell of elastomeric material defined by a convex front section configured in the shape of a female breast and a concave rear section, said front and rear sections joining each other along a generally circular periphery to define a fluid-tight sealed cavity, said concave rear section defining an air chamber when placed over a wearer's chest wall in the region of a removed breast to reduce chaffing promote air circulation and provide an air cushion between the underlying chest wall and said prosthesis in the region of said removed breast,
   a liquid contained within said cavity having a density approximately that of a natural breast,
   an upper flap extending upwardly from said periphery of said shell, said flap configured to cover subclavicular defects resulting from a mastectomy when said concave rear section is disposed over a wearer's chest in the region of a removed breast,
   first and second lateral flaps extending laterally from said shell periphery in opposite directions symmetrically relative to said upper flap to facilitate use of said prosthesis as a substitute for both left and right breasts,
   said first and second flaps configured to respectively cover lateral and sternum defects resulting from a mastectomy when said concave rear section is disposed over a wearer's chest in the region of a removed breast,
   each of said flaps being removable in whole and/or in part for tailoring the coverage provided by said flaps to the subclavicular, sternum and lateral defects of the wearer without destroying the fluid-tight chamber of said sealed cavity and the air circulation, antichaffing and cushioning action provided by said air chamber.

16. The prosthesis of claim 15 further including a lower flap extending downwardly from said shell periphery a distance sufficient to become sandwiched between said chest wall and the lower edge of a bra cup containing said liquid-filled shell for inhibiting said prosthesis from riding up on the wearer's chest.

17. The prosthesis of claim 15 wherein said flaps are fabricated of silicone, and have their rear exterior surfaces covered with acrylic to promote adhesion of said prosthesis to the chest wall of a wearer with double-sided nonsilicone adhesive tape.

18. The breast prosthesis of claim 15 wherein said rear concave section has a depth of approximately 1 cm at its center.

19. The breast prosthesis of claim 15 wherein said convex section is fabricated of silicone and has a first protuberance to simulate a nipple, said prosthesis further incluidng a thin convex silicone overlay sheet having a curvature approximating that of said convex front section in the region of said first protuberance and having a size corresponding to that of a normal areola, said overlay sheet having a hollow second protuberance in the central portion thereof which is larger than said first protuberance, said overlay intimately contacting said front convex section, to which is coheres without adhesive, only in a small annular region surrounding said first protuberance corresponding to the areola of a nipple, with said hollow second protuberance overlying said first protuberance to provide said convex section with an enlarged nipple.

20. The prosthesis of claim 19 wherein said overlay is air pervious in the region of said hollow second protuberance to permit it to collapse when a force is applied thereto and return to its normal shape when said force is removed.

21. The breast prosthesis of claim 15 wherein said convex front section is fabricated of silicone, said prosthesis further including a thin convex generally circular silicone overlay sheet having a diameter approximating that of a normal areola and a curvature approximating that of said convex front section in the region corresponding to the location of a normal areola, said overlay having a protuberance in the central portion thereof, said overlay intimately contacting said front convex section, to which it coheres without adhesive, in the region of a normal nipple and areola.

22. The prosthesis of claim 21 wherein said protuberance is hollow and air pervious to permit it to collapse when a force is applied thereto and return to its normal shape when said force is removed.

23. The prosthesis of claim 21 wherein said overlay has a thickness in the approximate range of 1–5 mils.

24. A breast prosthesis of claim 16 wherein said front convex section has a thickness in the approximate range of 1–5 mils, allowing it to produce an acute angle with said lower flap, simulating the sag of a normal breast.

* * * * *